US012799051B2

(12) United States Patent
Paul et al.

(10) Patent No.: US 12,799,051 B2
(45) Date of Patent: Nov. 17, 2026

(54) ENERGY-EFFICIENT PROCESS FOR SEPARATION OF 1-BUTENE FROM A HYDROCARBON STREAM USING A HEAT TRANSFER MEDIUM

(71) Applicant: Evonik Oxeno GmbH & Co. KG, Marl (DE)

(72) Inventors: Niklas Paul, Marl (DE); Armin Matthias Rix, Marl (DE); Moritz Schröder, Muenster (DE); Tanita Valèrie Six, Dortmund (DE); Tanja Steenweg, Dortmund (DE); Wim Mellaerts, Hoevenen (BE); Johannes Knossalla, Everswinkel (DE); Stephan Peitz, Oer-Erkenschwick (DE); Guido Stochniol, Haltern am See (DE); Tobias Laiblin, Brasschaat (BE)

(73) Assignee: Evonik Oxeno GmbH & Co. KG, Marl (DE)

( * ) Notice: Subject to any disclaimer, the term of this patent is extended or adjusted under 35 U.S.C. 154(b) by 139 days.

(21) Appl. No.: 18/957,961

(22) Filed: Nov. 25, 2024

(65) Prior Publication Data

US 2025/0171383 A1 May 29, 2025

(30) Foreign Application Priority Data

Nov. 29, 2023 (EP) .................................... 23213041

(51) Int. Cl.
*C07C 7/04* (2006.01)
*C07C 7/00* (2006.01)

(52) U.S. Cl.
CPC ................ *C07C 7/04* (2013.01); *C07C 7/005* (2013.01)

(58) Field of Classification Search
CPC ......... C07C 7/04; C07C 7/005; B01D 1/2856; B01D 3/007; B01D 3/143
See application file for complete search history.

(56) References Cited

U.S. PATENT DOCUMENTS

| | | | |
|---|---|---|---|
| 8,002,952 B2 | 8/2011 | Sechrist | |
| 10,774,020 B2 | 9/2020 | Di Girolamo et al. | |
| 2007/0149839 A1 | 6/2007 | Rix et al. | |
| 2017/0166497 A1 | 6/2017 | Kim et al. | |
| 2020/0207687 A1 * | 7/2020 | Kim | C10G 7/08 |

(Continued)

FOREIGN PATENT DOCUMENTS

| | | |
|---|---|---|
| CN | 112358375 | 2/2021 |
| DE | 10 2005 062 700 | 7/2007 |

(Continued)

OTHER PUBLICATIONS

Paul et al., U.S. Appl. No. 18/958,063, filed Nov. 25, 2024.

(Continued)

*Primary Examiner* — Ellen M Mcavoy
(74) *Attorney, Agent, or Firm* — Grüneberg Global IP, PLLC

(57) ABSTRACT

A process separates 1-butene from a C4 hydrocarbon stream having at least 1-butene, 2-butene, n-butane and isobutane in a separation unit with at least two distillation columns DK1 and DK2, wherein the heat of condensation is rendered utilizable by a heat transfer medium W in order to save energy costs and reduce $CO_2$ emission.

15 Claims, 4 Drawing Sheets

(56) References Cited

U.S. PATENT DOCUMENTS

| | | | | |
|---|---|---|---|---|
| 2020/0216376 | A1 | 7/2020 | Peitz et al. | |
| 2021/0363075 | A1* | 11/2021 | Kim | C10G 7/00 |
| 2024/0059633 | A1* | 2/2024 | Lutze | B01D 3/143 |
| 2025/0171384 | A1 | 5/2025 | Paul et al. | |
| 2025/0171385 | A1 | 5/2025 | Paul et al. | |
| 2025/0171386 | A1* | 5/2025 | Paul | C07C 7/005 |

FOREIGN PATENT DOCUMENTS

| | | | |
|---|---|---|---|
| EP | 2 875 850 | A1 | 5/2015 |
| EP | 3 626 804 | A2 | 3/2020 |
| EP | 3 680 224 | | 7/2020 |
| EP | 3 626 804 | B1 | 2/2022 |

OTHER PUBLICATIONS

Paul et al., U.S. Appl. No. 18/958,116, filed Nov. 25, 2024.
U.S. Appl. No. 18/958,063, filed Nov. 25, 2024, Paul et al.
U.S. Appl. No. 18/958,116, filed Nov. 25, 2024, Paul et al.
European Search Report received for European Patent Application No. 23213041.9, mailed on May 31, 2024, 6 pages.
U.S. Office Action dated Jun. 29, 2026, in U.S. Appl. No. 18/958,063, 12 pages.
U.S. Office Action dated Jun. 11, 2026, in U.S. Appl. No. 18/958,116, 13 pages.

* cited by examiner

ENERGY-EFFICIENT PROCESS FOR SEPARATION OF 1-BUTENE FROM A HYDROCARBON STREAM USING A HEAT TRANSFER MEDIUM

CROSS-REFERENCE TO RELATED APPLICATIONS

This patent application claims priority to European Patent Application No. 23213041.9, filed on Nov. 29, 2023, in the European Patent Office, the entire disclosure of which is hereby incorporated by reference herein.

BACKGROUND OF THE INVENTION

Field of the Invention

The present invention relates to a process for separating 1-butene from a C4 hydrocarbon stream containing at least 1-butene, 2-butene, n-butane and isobutane in a separation unit comprising at least two distillation columns DK1 and DK2, wherein the heat of condensation is rendered utilizable by means of a heat transfer medium in order to save energy costs and reduce $CO_2$ emission. 1-Butene can be obtained in large amounts from technical C4 hydrocarbon streams, for example the C4 cut from steamcrackers or FCC units. These C4 hydrocarbon streams consist essentially of butadiene, the monoolefins isobutene, 1-butene and the two 2-butenes (cis- and trans-2-butene), and the saturated hydrocarbons isobutane and n-butane. Because of the small differences in the boiling points of the constituents, the low separation factors thereof and the formation of azeotropes, exclusively distillative workup of C4 hydrocarbon streams is difficult and uneconomic.

Typically, therefore, the butadiene is first separated off by extractive distillation or hydrogenated selectively to butenes. What remains in each case is a C4 hydrocarbon stream (called raffinate 1) containing not only the saturated hydrocarbons n-butane and isobutane but also the olefins isobutene, 1-butene and 2-butenes, while the butadiene is present in small amounts at most.

Since the boiling points of 1-butene and isobutene are close to one another, it is generally not possible to economically separate 1-butene from corresponding C4 hydrocarbon streams via simple distillation. The isobutene is therefore removed as far as possible, for example via an MTBE or ETBE synthesis. The removal of the isobutene gives rise to a C4 hydrocarbon stream (called raffinate 2) containing the linear butenes (1- and 2-butenes) and the saturated hydrocarbons isobutane and n-butane.

Description of Related Art

The separation of 1-butene from such C4 hydrocarbon streams is possible and is used in the chemical industry. This separation is effected in a distillation unit comprising at least two distillation columns. Isobutane and 1-butene are obtained at the top of the first distillation column and directed to the second distillation column. Then isobutane and 1-butene are separated from one another in the second distillation column. Such a process is disclosed, for example, in DE 10 2005 062 700 A1.

In the known processes, the energy needed for the separation of the C4 hydrocarbon stream is typically introduced into the bottom of the two distillation columns via heating steam. Heating steam is generally available at chemical production sites. In the volumes needed for the separation tasks in question, the use of heating steam means a cost factor that cannot be underestimated. Moreover, recycling of the spent heating steam is not always simple in logistic terms since the steam can only be returned within certain specifications (pressure, temperature, or the like). Furthermore, the generation of heating steam generates a large volume of $CO_2$.

SUMMARY OF THE INVENTION

It was therefore an object of the present invention to provide a process in which energy and $CO_2$ emission can be saved by comparison with the known processes and which can be integrated into existing plants.

DETAILED DESCRIPTION OF THE INVENTION

Figure 1:
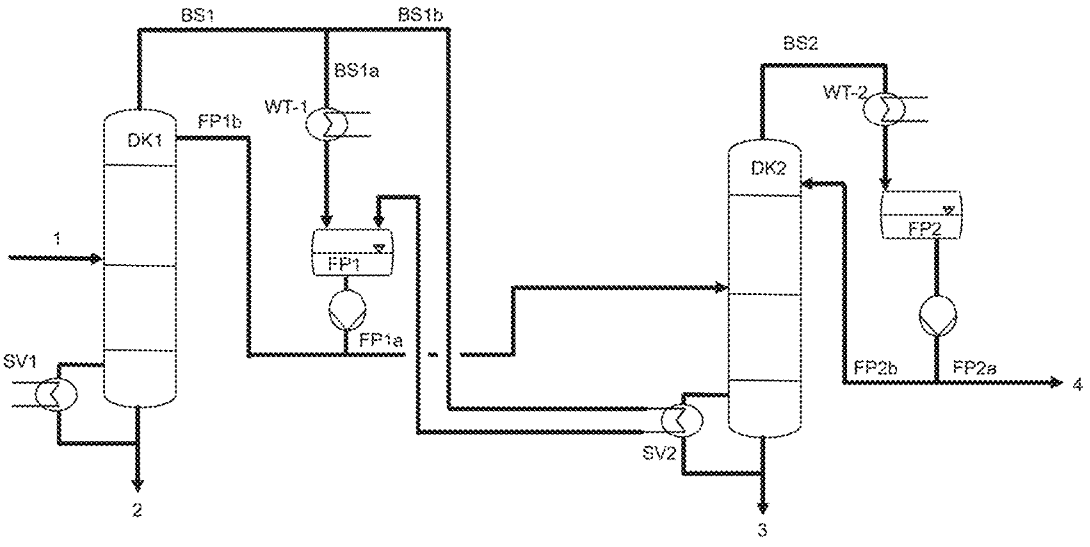
FIG. 1 shows a configuration according to a conventional dual pressure circuit (see Example 1).

This problem is solved by the embodiment of the process proposed in the description herein. Preferred embodiments are also specified in the dependent embodiments. The process according to the invention is a process for separating 1-butene from a raffinate 2 stream containing at least 1-butene, 2-butene, n-butane and isobutane in a separation unit comprising at least two distillation columns DK1 and DK2, wherein

- the first distillation column DK1 has at least one reboiler SV1 and the second distillation column DK2 has at least one reboiler SV2;
- the reboiler SV1 is fed with a stream which is withdrawn at the lower end of DK1 and, after passing through the respective reboiler, is guided back to DK1;
- the reboiler SV2 is fed with a stream which is withdrawn at the lower end of DK2 and, after passing through the respective reboiler, is guided back to DK2; where the process comprises the following steps:

(a) the raffinate 2 stream is directed to the first distillation column DK1 and separated in DK1 into at least one vapour stream BS1 which comprises at least 1-butene and isobutane and is withdrawn at the top of DK1, and at least one bottom stream which comprises at least 1-butene and 2-butene and is withdrawn at the bottom of DK1;

(b) the vapour stream is separated into at least two substreams BS1*a* and BS1*b;*

(c) energy is transferred from BS1*a* to a liquid or gaseous heat transfer medium W, giving rise to a heat transfer medium W1;

(d) a portion BS1*b* of the vapour stream BS1 other than BS1*a* is conducted to the reboiler SV2, where energy is transferred from BS1*b* to the stream in the reboiler SV2;

(e) streams BS1*a* and BS1*b* are directed at least partly to the second distillation column DK2 and separated in DK2 into at least one vapour stream BS2 which comprises at least isobutane and is withdrawn at the top of DK2, and at least one product stream which comprises at least 1-butene and is withdrawn at the bottom of DK2;

(f) energy is transferred from BS2 to a liquid or gaseous heat transfer medium W, giving rise to a heat transfer medium W2;

(g) at least a portion of the heat transfer medium W2 is compressed, giving rise to a compressed heat transfer medium W2.1 at a higher pressure than heat transfer medium W2;

(h) heat transfer medium W1 is mixed with heat transfer medium W2.1, giving rise to a mixed heat transfer medium W3;

(i) at least a portion of the mixed heat transfer medium W3 is compressed, giving rise to a compressed heat transfer medium W3.1 at a higher pressure than the mixed heat transfer medium W3;

(j) energy is transferred from the compressed heat transfer medium W3.1 to the stream in reboiler SV1.

One advantage of the process according to the invention is heat integration via at least one heat transfer medium, by which energy is transferred in the reboiler SV1 to the stream present therein and hence energy is introduced into the bottom. The result of the energy transfer in the reboiler SV1 in the first distillation column DK1 is that less heating steam, if any at all, has to be used for heating of distillation column DK1. Since the reboiler SV2 can also be operated with a portion of the vapour, it is possible to achieve (almost) complete electrification of the energy-intensive process, which in turn enables the use of green power. This saves considerable amounts of energy costs and $CO_2$ emission.

According to the present invention, the starting stream from which the 1-butene is to be separated is a raffinate 2 stream containing at least 1-butene, 2-butene, n-butane and isobutane. Corresponding streams are available on the market, for example as a C4 cut from steamcrackers or FCC units. It has already been mentioned in the introduction that raffinate 2 is formed by removal of polyunsaturated C4 hydrocarbons, especially butadiene, and isobutene from the stream. Complete removal is not possible in many cases for economic and technical reasons.

However, the amounts of polyunsaturated C4 hydrocarbons, especially butadiene, and isobutene should be at a minimum.

The raffinate 2 used preferably contains less than 1000 ppm, preferably less than 500 ppm, of isobutene. If higher amounts of isobutene are present in the starting stream, it would be possible for an MTBE or ETBE synthesis (methyl tert-butyl ether=MTBE/ethyl tert-butyl ether=ETBE) to be effected between the two distillation columns DK1 and DK2, in order to react the isobutene with methanol (for MTBE) or ethanol (ETBE) and then to separate off the MTBE or ETBE. It is thus possible to greatly reduce the concentration of isobutene upstream of the second distillation column DK2. This is because isobutene would be obtained in the bottom in the second distillation column and hence in the 1-butene.

Further preferably, the raffinate 2 used in the process of the present invention contains less than 4% by weight of polyunsaturated C4 hydrocarbons. In a particularly preferred embodiment, the concentration of the polyunsaturated C4 hydrocarbons should be less than 500 ppm. If the streams should contain higher amounts of butadiene, it would be possible to conduct a selective hydrogenation beforehand, in which the butadiene is converted to butenes and/or butanes. Corresponding processes are known to the person skilled in the art, for example from EP 3 680 224 A1.

The raffinate 2 stream used may additionally contain certain amounts of water, especially in an amount of 150 to 4000 ppm. It is preferable that the water is at least partly separated off by the process described here. The water will accumulate in the respective vapour stream BS1 and BS2 in each of the two distillation columns DK1 and DK2 and be obtained as a second liquid phase after condensation, which can be separated off via udders in the distillate vessels of DK1 and/or DK2.

The bottom products of DK1 and of DK2 feature very low contents of butadiene and water, preferably each below 100 ppm, more preferably below 5 ppm.

The process according to the invention is conducted in a separation unit comprising at least the two distillation columns DK1 and DK2. DK1 is the first distillation column and has at least one reboiler SV1. DK2 is the second distillation column and has at least one reboiler SV2. In a preferred embodiment, the distillation column has only the reboiler SV1. It is additionally preferable that the distillation column DK1 has only the one reboiler SV2. The pressures in the two distillation columns DK1 and DK2 should in particular have to be chosen such that heat can be transferred in the reboilers. The terms “first distillation column”, “distillation column DK1” and “DK1” should be considered to be synonymous in the context of the present invention. The terms “second distillation column”, “distillation column DK2” and “DK2” should likewise be considered to be synonymous in the context of the present invention.

The energy needed for the separation task is introduced into the first distillation column DK1 via the reboiler SV1. The reboiler SV1 is fed with a stream which is withdrawn at the lower end of DK1 and, after passing through the respective reboiler, is guided back to DK1. The stream is heated as it passes through the reboiler SV1.

The situation is comparable for the reboiler SV2 of the second distillation column DK2, by means of which energy needed for the separation task is introduced. For this purpose, the reboiler SV2 is fed with a stream which is withdrawn at the lower end of DK2 and, after passing through the respective reboiler, is guided back to DK2. The stream is heated as it passes through the reboiler SV2 and at least partly evaporates as it does so.

According to the invention, “reboilers” refer to evaporators that heat the bottom of the respective distillation column. Such a reboiler is typically disposed outside the respective distillation column. Since reboilers transfer energy, in particular heat, from one stream to another, they are heat transferrers. The stream to be evaporated is drawn off from the bottom of the distillation column via a draw and fed to the reboiler. The evaporated stream, with or without a residual proportion of liquid, is returned back to the respective distillation column in the region of the bottom via at least one feed.

Suitable evaporators that can be used as reboilers are, for example, natural circulation evaporators, forced circulation evaporators, forced circulation flash evaporators, kettle evaporators, falling-film evaporators or thin-film evaporators. Heat exchangers for the evaporator that are typically used in the case of natural circulation evaporators and forced circulation evaporators are a shell-and-tube or plate apparatus. As well as those mentioned, it is alternatively possible to use any other design of evaporator which is known to those skilled in the art and is suitable for use in a distillation column.

The raffinate 2 which is directed to the first distillation column DK1 is separated in distillation column DK1 into at least two streams, i.e. at least one vapour stream BS1 which comprises at least 1-butene and isobutane and is withdrawn at the top of DK1, and at least one bottom stream which comprises at least 1-butene and 2-butene and is withdrawn at the bottom of DK1. This bottom stream can be guided to an oligomerization. The vapour stream BS1 can also be withdrawn at the top of the distillation column in the form of multiple substreams BS1*n* where n is an integer and is equal to the number of substreams. The same also applies to the bottom stream. The temperature at the bottom of the first distillation column DK1 is preferably in the range from 40 to 110 °C, preferably 50 to 100 °C.

In principle, the raffinate 2 stream can be directed into the first distillation column DK1 via one or more feed points. If there are multiple feed points for the raffinate 2 stream, multiple separate streams are accordingly directed into the distillation column. In the embodiments of the present invention in which the raffinate 2 stream is directed into the distillation column DK1 as two or more separate streams, it is advantageous when the feed points of the individual streams are essentially at the same height on the distillation column DK1.

The pressure and temperature of the vapour stream BS1 are specified hereinafter. This relates in particular to the pressure and temperature of the at least one vapour stream BS1 when it is withdrawn from distillation column DK1. The pressure of the vapour stream BS1 is especially in the range from 6 to 15 bar absolute, preferably in the range from 7.5 to 13 bar absolute. The temperature of the vapour stream BS1 is especially in the range from 45 °C to 120 °C, preferably in the range from 48 °C to 100 °C, further preferably in the range from 50 °C to 90 °C, further preferably in the range from 55 °C to 80 °C, more preferably in the range from 60 °C to 80 °C.

The distillation column DK1 used for the separation of the raffinate 2 stream may be any distillation column known to the person skilled in the art. Distillation column DK1 preferably contains internals. Suitable internals are for example trays, unstructured packings (random packings) or structured packings. Trays used are typically bubble-cap trays, sieve trays, valve trays having fixed or movable valves, tunnel-cap trays or slotted trays. Unstructured packings are generally beds of random packings. Random packings used are typically Raschig rings, Pall rings, Berl saddles, Super-Rings/Super-Rings Plus or Intalox® saddles. Structured packings are sold for example under the Mellapak® trade name by Sulzer. In addition to the internals mentioned, further suitable internals are known to those skilled in the art and may likewise be used.

Preferred internals have a low specific pressure drop per theoretical plate. Structured packings and random packings have, for example, a significantly lower pressure drop per theoretical plate than trays. This has the advantage that the pressure drop in distillation column DK1 remains as low as possible and hence the mechanical output of the compressor and the temperature of the raffinate 2 stream to be evaporated remains low.

In a particularly preferred embodiment of the present invention, distillation column DK1 comprises a multitude of trays, preferably between 150 and 300 trays, further preferably between 170 and 220 trays.

What is meant in the context of the present invention by the withdrawal of the at least one vapour stream BS1 comprising at least 1-butene and isobutane at the top of distillation column DK1 is in particular that the at least one vapour stream BS1 is withdrawn as top stream or as side draw above the internals in distillation column DK1.

What is meant in the context of the present invention by the withdrawal of the at least one bottom stream comprising at least 1-butene and 2-butene at the bottom of distillation column DK1 is in particular that the at least one bottom stream is withdrawn directly at the bottom or at the lower tray of distillation column DK1.

Distillation column DK1 is preferably operated with reflux. What is meant by "reflux" is that the vapour stream BS1 withdrawn at the top end of distillation column DK1 is at least partly fed back to distillation column DK1. In the cases where such a reflux is established, the reflux ratio is preferably 2 to 30, more preferably 5 to 20, especially preferably 8 to 15.

A reflux can be established by mounting a condenser at the top of distillation column DK1. Vapour stream BS1 is partly condensed in the condenser and fed back to distillation column DK1. The vapour stream or a portion thereof can also be applied as reflux to the distillation column only after compression and expansion. In general and in the context of the present invention, a reflux ratio means the ratio of the proportion of the mass flow rate withdrawn from the column (kg/h) that is returned back into the column in liquid form (reflux) to the proportion of that mass flow rate (kg/h) which is discharged from the respective column in liquid form or gaseous form.

After the withdrawal of vapour stream BS1, the vapour stream BS1 is separated in step (b) into at least two substreams BS1*a* and BS1*b*. The separation can in principle be effected in a known manner, for example by means of a splitter (with closed-loop control using a compressor and/or an adjuster valve). Another conceivable option here would be closed-loop control via which the mass flow rates of BS1*a* and BS1*b* are adjusted as a function of a particular parameter.

Subsequently, in step (c), energy is transferred from substream BS1*a* to a liquid or gaseous heat transfer medium W, giving rise to a heat transfer medium W1. The energy to be transferred in this case is preferably heat, and the result is a heated heat transfer medium W1. The transfer of energy to the heat transfer medium W will reduce the energy content of BS1*a*, i.e. the stream will cool down and/or condense.

The heat transfer medium W utilized may be any working medium familiar to the person skilled in the art. The heat transfer medium W is preferably selected from the group consisting of water; alcohols; alcohol-water mixtures; salt-water solutions; ammonia; mineral oils, for example diesel oils; thermal oils, for example silicone oils; biological oils, for example limonene; and aromatic or aliphatic hydrocarbons, for example dibenzyltoluene, further preferably water, methanol, ethanol, propanol, n-pentane, n-butane, n-hexane, n-propane or ammonia, more preferably water.

If the heat transfer medium W is used in step (c) in the liquid phase, i.e. a liquid heat transfer medium W, and this is supplied in step (c) with energy, preferably heat, the heat transfer medium W will at least partly evaporate and hence a gaseous heat transfer medium W1 will be obtained. If the heat transfer medium W is used in step (c) in the gaseous phase, i.e. a gaseous heat transfer medium W, and this is supplied in step (c) with energy, preferably heat, a gaseous heat transfer medium W1 will likewise be obtained.

The wording "liquid heat transfer medium" in the context of the present invention means that >50% by weight, further preferably >55% by weight, further preferably >75% by weight, further preferably >90% by weight and more preferably >99% by weight of the heat transfer medium used in step (c) is in the liquid state of matter, based in each case on the total weight of the heat transfer medium used in step (c).

The wording "gaseous heat transfer medium" in the context of the present invention means that >30% by weight, further preferably >50% by weight, further preferably >75% by weight, further preferably >90% by weight and more preferably >99% by weight of the heat transfer medium used in step (c) is in the gaseous state of matter, based in each case on the total weight of the heat transfer medium used in step (c).

The transfer of energy in step (c) can be performed by processes known to the person skilled in the art or with heat exchangers known to the person skilled in the art, for example the evaporators already mentioned. The heat exchanger in this case may also be the condenser for condensation of BS1*a*. This has the advantage that there is no need to install an additional condenser.

After the described transfer of energy in step (c), the heat transfer medium W1 preferably has an elevated temperature and/or an elevated pressure compared to the heat transfer medium W. In a preferred embodiment of the present invention, W1 is preferably at a temperature in the range from 30 °C to 80 °C. The pressure of W1 is preferably in the range from 1 bar to 20 bar, preferably 3 bar to 12 bar.

It will be apparent that the heat transfer medium W1 corresponds to the heat transfer medium W, and W and W1 differ solely in their respective pressure and/or temperature, and, as the case may be, when W has been used in liquid form, by the state of matter.

In step (d) of the process according to the invention, at least a portion BS1*b* of the vapour stream BS1 other than BS1*a* is conducted to the reboiler SV2, where energy is transferred in the reboiler SV2 from BS1*b* to the stream present in the reboiler. Step (d) lowers the energy of BS1*b*, such that BS1*b* is preferably at least partly condensed.

The transfer of energy from BS1*b* to the stream in the reboiler SV2, preferably the heating of the stream in the reboiler SV2 by BS1*b*, is preferably direct. What is meant by direct transfer is that BS1*b* and the stream in SV2 do not come into direct contact, but energy, especially heat, is transferred from BS1*b* to the stream in SV2 without the presence of any additional heat transfer medium. Reboilers SV2 used may be the heat transferrers or heat exchangers that are familiar to the person skilled in the art, especially evaporators already mentioned above.

Once streams BS1*a* and BS1*b* have undergone energy transfer to the heat transfer medium W or passed through the reboiler SV2 and transferred energy to the respective streams, these streams BS1*a* and BS1*b*, in step (e), are at least partly directed to the second distillation column DK2, where the separation between isobutane and 1-butene is then effected in order to obtain a 1-butene stream of maximum purity. The separation is effected in DK2 into at least one vapour stream BS2 which comprises at least isobutane and is withdrawn at the top of DK2, and at least one product stream which comprises at least 1-butene and is withdrawn at the bottom of DK2. The two streams BS1*a* and BS1*b* may independently be guided as separate feed streams or collectively to the second distillation column DK2.

Before the streams are guided to the second distillation column by step (e) to the second distillation column, streams BS1*a* and BS1*b*, in a preferred embodiment, are guided to a flash vessel and expanded therein to obtain a liquid phase FP1 of streams BS1*a* and BS1*b*. The flash vessel may additionally comprise a condenser in order to condense a portion of the gaseous phase obtained.

In a preferred embodiment of the present invention, streams BS1*a* and BS1*b* are guided collectively to the second distillation column. For this purpose, the two streams are in particular brought to the same pressure and the same temperature. Thus, if streams BS1*a* and BS1*b* are to be conducted collectively to the distillation column, it is preferable that streams BS1*a* and BS1*b* are combined in a flash vessel and are obtained as a common liquid phase FP1.

At least a portion FP1*a* of the liquid phase FP1 is then directed in step (e) to distillation column DK2. For this purpose, in a particularly preferred embodiment, a pump is used. It is possible here to use pumps known to the person skilled in the art. Suitable pumps are, for example, standard chemical pumps.

It is further preferable that a portion FP1*b* of the liquid phase FP1 other than FP1*a* is returned as reflux to the first distillation column DK1. It is particularly preferable that this transfers energy from stream FP1*b* to the raffinate 2 stream before the raffinate 2 stream is introduced into the first distillation column DK1. This preheats the raffinate 2 stream. This is energetically advantageous because less energy has to be introduced for the separation task via the reboilers. The transfer of energy from FP1*b* to the raffinate 2 stream, preferably the heating of the raffinate 2 stream by FP1*b*, is preferably direct, i.e. without use of a (further) heat transfer medium. For this purpose, it is possible to use heat transferrers or evaporators that are familiar to the person skilled in the art, as described above.

In the second distillation column DK2, the streams that both respectively comprise at least isobutane and 1-butene are separated in step (e) into at least one vapour stream BS2 which comprises at least isobutane and is withdrawn at the top of DK2, and at least one product stream which comprises at least 1-butene and is withdrawn at the bottom of DK2.

The distillation column DK2 used for the separation of the two streams VB1 and BS1*b* or FP1*a* may be any distillation column known to the person skilled in the art. Distillation column DK2 preferably contains internals. Suitable internals are for example trays, unstructured packings (random packings) or structured packings. Trays used are typically bubble-cap trays, sieve trays, valve trays having fixed or movable valves, tunnel-cap trays or slotted trays. Unstructured packings are generally beds of random packings. Random packings used are typically Raschig rings, Pall rings, Berl saddles, Super-Rings/Super-Rings Plus or Intalox® saddles. Structured packings are sold for example under the Mellapak® trade name by Sulzer. In addition to the internals mentioned, further suitable internals are known to those skilled in the art and may likewise be used.

Preferred internals have a low specific pressure drop per theoretical plate. Structured packings and random packings have, for example, a significantly lower pressure drop per theoretical plate than trays. This has the advantage that the pressure drop in distillation column DK2 remains as low as possible and hence the mechanical output of the compressor and the temperature of the two streams BS1*a* and BS1*b* or FP1*a* to be evaporated remains low.

In a particularly preferred embodiment of the present invention, the second distillation column DK2 comprises a multitude of trays, preferably between 150 and 300 trays, further preferably between 170 and 220 trays.

What is meant in the context of the present invention by the withdrawal of the at least one vapour stream BS2 comprising at least isobutane at the top of distillation column DK2 is in particular that the at least one vapour stream BS2 is withdrawn as top stream or as side draw above the internals in distillation column DK2.

What is meant in the context of the present invention by the withdrawal of the at least one product stream comprising at least 1-butene at the bottom of distillation column DK2 is in particular that the at least one product stream is withdrawn directly at the bottom or at the lower tray of distillation column DK2. The product stream preferably contains at least 99% by weight of 1-butene, further preferably at least 99.5% by weight of 1-butene, more preferably at least 99.6% by weight of 1-butene. The 1-butene is the target product of the present process, and therefore the product stream is discharged from the process. The 1-butene may be used, for example, as a comonomer in the production of polyethylene.

It should be noted here that the separation sharpness in the first distillation column DK1 ultimately determines the purity of the 1-butene in the product stream which is withdrawn from the second distillation column DK2. This is because butane is likewise obtained as a high boiler in DK2, and therefore with the 1-butene. This would contaminate the 1-butene. It should thus be ensured that the separation of the raffinate 2 stream in DK1 is run such that barely any butane gets to DK2. It is therefore preferable that the stream guided to DK2 (BS1*a* and BS1*b* or FP1*a*) contains not more than between 500 and 900 ppm of butanes, based on the total amount of the stream.

The temperature at the bottom of the second distillation column DK2 during the process according to the invention is preferably in the range from 30 to 100 °C, preferably 45 to 80 °C. Further preferably, the pressure at the top of the second distillation column DK2 is in the range from 3 to 12 bar absolute, preferably 5 to 10 bar absolute.

Distillation column DK2 can also be operated with reflux. What is meant by "reflux" is that the vapour stream BS2 withdrawn at the top end of distillation column DK2 is at least partly fed back to distillation column DK2. In the cases where such a reflux is established, the reflux ratio is preferably 10 to 80, especially preferably 30 to 50.

A reflux can be established by mounting a condenser at the top of distillation column DK2. Vapour stream BS2 is partly condensed in the condenser and fed back to distillation column DK2. In general and in the context of the present invention, a reflux ratio means the ratio of the proportion of the mass flow rate withdrawn from the column (kg/h) that is returned back into the column in liquid form (reflux) to the proportion of that mass flow rate (kg/h) which is discharged from the respective column in liquid form or gaseous form.

The vapour stream BS2 obtained in distillation column DK2 is used for thermal integration. In step (f), energy is transferred from BS2 to a liquid or gaseous heat transfer medium W, giving rise to a heat transfer medium W2. The energy to be transferred in this case is preferably heat, and the result is a heated heat transfer medium W2. The transfer of energy to the heat transfer medium W will reduce the energy content of BS2, i.e. the stream will cool down and/or condense.

The heat transfer medium W utilized may be any working medium familiar to the person skilled in the art. The heat transfer medium W is preferably selected from the group consisting of water; alcohols; alcohol-water mixtures; salt-water solutions; ammonia; mineral oils, for example diesel oils; thermal oils, for example silicone oils; biological oils, for example limonene; and aromatic or aliphatic hydrocarbons, for example dibenzyltoluene, further preferably water, methanol, ethanol, propanol, n-pentane, n-butane, n-hexane, n-propane or ammonia, more preferably water. The heat transfer medium W which is used in steps (c) and (f) is preferably identical. It is particularly preferable that there is a heat transfer medium circuit in which the heat transfer medium W passes through steps (c) and (f) to (j).

If the heat transfer medium W is used in step (f) in the liquid phase, i.e. a liquid heat transfer medium W, and this is supplied in step (f) with energy, preferably heat, the heat transfer medium W will at least partly evaporate and hence a gaseous heat transfer medium W2 will be obtained. If the heat transfer medium W is used in step (f) in the gaseous phase, i.e. a gaseous heat transfer medium W, and this is supplied in step (f) with energy, preferably heat, a gaseous heat transfer medium W2 will likewise be obtained.

The wording "liquid heat transfer medium" in the context of the present invention means that >50% by weight, further preferably >55% by weight, further preferably >75% by weight, further preferably >90% by weight and more preferably >99% by weight of the heat transfer medium used in step (f) is in the liquid state of matter, based in each case on the total weight of the heat transfer medium used in step (f).

The wording "gaseous heat transfer medium" in the context of the present invention means that >30% by weight, further preferably >50% by weight, further preferably >75% by weight, further preferably >90% by weight and more preferably >99% by weight of the heat transfer medium used in step (f) is in the gaseous state of matter, based in each case on the total weight of the heat transfer medium used in step (f).

The transfer of energy in step (f) can be performed by processes known to the person skilled in the art or with heat exchangers known to the person skilled in the art, for example the evaporators already mentioned. The heat exchanger in this case may also be the condenser for condensation of BS2. This has the advantage that there is no need to install an additional condenser.

After the described transfer of energy in step (f), the heat transfer medium W2 preferably has an elevated temperature and/or an elevated pressure compared to the heat transfer medium W. In a preferred embodiment of the present invention, W1 is preferably at a temperature in the range from 30 °C to 80 °C. The pressure of W2 is preferably in the range from 1 bar to 20 bar, preferably 2 bar to 8 bar. In a preferred embodiment of the present invention, the pressure and/or temperature of the heat transfer medium W2 is less than the pressure and/or temperature of the heat transfer medium W1.

Once energy has been transferred in step (f) from vapour stream BS2 to the heat transfer medium, BS2 can be discharged from the process as isobutane stream IB1. But before BS2 is removed from the process as IB1, stream VB2, in a preferred embodiment of the present invention, is guided to a flash vessel and expanded therein to obtain a liquid phase FP2. The flash vessel may additionally comprise a condenser in order to condense a portion of the gaseous phase obtained.

At least a portion FP2*a* of the liquid phase FP2 can then be discharged from the process as isobutane stream IB1. For this purpose, in a particularly preferred embodiment, a pump is used. Under some circumstances and given a sufficient pressure ratio, it would also be possible that no pump is used. If a pump is used, it is possible to use pumps known to the person skilled in the art. Suitable pumps are, for example, standard chemical pumps. It is further preferable that a portion FP2*b* of the liquid phase FP1 other than FP2*a* is returned as reflux to the first distillation column DK2.

In the subsequent step (g), at least a portion of the heat transfer medium W2 is compressed, giving rise to a heat transfer medium W2.1 that has been compressed relative to W2 and is at a higher pressure than heat transfer medium W2. The pressure of W2.1 after the compression is preferably in the range from 1 bar to 20 bar, preferably 3 bar to 12 bar. Further preferably, the pressure of the compressed heat transfer medium W2.1 and of heat transfer medium W1 is identical or varies by a maximum of ±10%.

The compressing of the at least one portion of heat transfer medium W2 in step (g) can be effected in any manner known to the person skilled in the art. For example, the compression can be performed mechanically and in a single-stage or multistage compression. What is meant by "single-stage" in this connection is that compression takes place from one pressure level to another. What is meant by "multistage" is that compression is effected first to a pressure level X and then from X to the pressure level Y. In a multistage compression, it is possible to use two or more compressors of the same type or compressors of different types. A multistage compression can be effected with one or more compressor machines. The use of single-stage compression or multistage compression depends on the compression ratio and hence on the pressure to which the heat transfer medium W2 is to be compressed.

The heat transfer medium W1 in step c) is preferably at a higher pressure than the heat transfer medium W2 in step f). The compression in step g) brings the heat transfer medium W2 to the same or a similar pressure by comparison with W1. The wording "similar pressure" in this connection means that the pressure of W1 and the pressure of the compressed heat transfer medium W2.1 after the compression differ by less than 5%, preferably by less than 1%.

A suitable compressor in the process according to the invention, especially for compression of the heat transfer medium W2, is any compressor known to the person skilled in the art, preferably mechanical compressor, with which gas streams can be compressed. Suitable compressors are, for example, single-stage or multistage geared turbocompressors, piston compressors, screw compressors, centrifugal compressors or axial compressors.

The compressed heat transfer medium W2.1, in the subsequent step (h), is mixed with heat transfer medium W1, giving rise to a mixed heat transfer medium W3. The mixing can be effected without any special internals simply by the merging of the two pipelines. This is fundamentally familiar to the person skilled in the art. The mixing of the two heat transfer media W2.1 and W1 has the advantage that superheating of heat transfer medium W1 can contribute to superheating of heat transfer medium W2.1. As a result, there is no need for any other heat exchanger to be present before the mixed heat transfer medium W3 is compressed in the subsequent step (i).

In the already mentioned step (i), at least a portion of the heat transfer medium W3 is compressed, giving rise to a heat transfer medium W3.1 that has been compressed relative to W3 and is at a higher pressure than heat transfer medium W3. The pressure of W3.1 after the compression is preferably in the range from 5 bar to 30 bar, preferably 10 bar to 20 bar.

The compressing of the at least one portion of heat transfer medium W3 in step (i) can be effected in any manner known to the person skilled in the art. For example, the compression can be performed mechanically and in a single-stage or multistage compression. What is meant by "single-stage" in this connection is that compression takes place from one pressure level to another. What is meant by "multistage" is that compression is effected first to a pressure level X and then from X to the pressure level Y. In a multistage compression, it is possible to use two or more compressors of the same type or compressors of different types. A multistage compression can be effected with one or more compressor machines. The use of single-stage compression or multistage compression depends on the compression ratio and hence on the pressure to which the heat transfer medium W3 is to be compressed.

A suitable compressor in the process according to the invention, especially for compression of the heat transfer medium W3, is any compressor known to the person skilled in the art, preferably mechanical compressor, with which gas streams can be compressed. Suitable compressors are, for example, single-stage or multistage geared turbocompressors, piston compressors, screw compressors, centrifugal compressors or axial compressors.

In step (j) of the process according to the invention, energy is transferred from the compressed heat transfer medium W3.1 to the stream in reboiler SV1. Step (j) lowers the energy of W3.1, such that W3.1 is preferably at least partly condensed. According to the invention, the phrase "transfer of energy" especially means "heating", i.e. transfer of energy in the form of heat.

The transfer of energy from W3.1 to the stream in the reboiler SV1, preferably the heating of the stream in the reboiler SV1 by W3.1, is preferably direct. What is meant by direct transfer is that, although W3.1 and the stream in SV1 do not come into direct contact, energy, especially heat, is transferred from W3.1 to the stream in SV1 without the presence of any additional heat transfer medium. Reboilers SV1 used may be the heat transferrers or heat exchangers that are familiar to the person skilled in the art, especially evaporators.

The transfer of energy in step (j) can be performed by processes known to the person skilled in the art or with heat exchangers known to the person skilled in the art. Suitable evaporators that can be used as heat exchangers are, for example, natural circulation evaporators, forced circulation evaporators, forced circulation flash evaporators, kettle evaporators, falling-film evaporators or thin-film evaporators. As well as those mentioned, it is alternatively possible to use any other design of evaporator which is known to those skilled in the art and is suitable for use in a distillation column.

In the basic configuration of the present invention, the two streams W2 and W3 are each compressed with a single compressor. In a preferred embodiment of the present invention, the two streams W2 and W3 are compressed in a single, preferably multistage, compressor. The number of stages necessary depends on the target compression ratio.

As mentioned, the heat transfer medium is preferably circulated. This means that the heat transfer medium W3.1, after transferring energy in step (j), is fed back and used again in steps (c) and (f). For this purpose, in a preferred embodiment of the present invention, only a single heat transfer medium is used throughout the process. The heat transfer medium W used in step (c) and in step (f) is thus identical. The heat transfer medium W3.1 can also be cooled before it is directed partly to step (c) and partly to step (f) as heat transfer medium W. The reason for this is that the heat transfer medium W that absorbs the thermal energy from the condensation of vapour streams BS1 and BS2 should preferably be at a particular pressure and temperature level in order to be able to absorb the desired amount of thermal energy in the heat exchangers. For this purpose, it may be necessary for the heat transfer medium W3.1, after the transfer of energy in the reboiler, to be cooled. In order to utilize this energy, the cooling can be effected in a heat exchanger by which the heat transfer medium W2 is preheated. This in turn can have the effect that less energy has to be introduced by the compressor(s).

After the transfer of energy in step (j) of the process according to the invention, the heat transfer medium W3.1 can be used to preheat the raffinate 2 stream before the raffinate 2 stream is directed into the first distillation column. Subsequently, the heat transfer medium W3.1 would be recycled after preheating and directed partly to step (c) and partly to step (f) as heat transfer medium W. If there is no preheating, the heat transfer medium W3.1 is recycled without this additional step and directed partly to step (c) and partly to step (f) as heat transfer medium W.

The thermal integration by means of the heat pump described here would also be combinable with other measures for thermal integration. It would also be possible here to provide one or more vapour compressions.

The present invention is hereinbelow elucidated with reference to figures. The figures are for illustration but are not to be understood as limiting.

FIG. 1 shows a configuration according to the prior art, a conventional dual pressure circuit (see Example 1). The raffinate 2 stream (1) is directed to the first distillation column DK1, where it is separated into a vapour stream BS1 which comprises at least 1-butene and isobutane and is withdrawn at the top of DK1, and a bottom stream (2) which comprises at least 1-butene and 2-butene and is withdrawn at the bottom of DK1. This stream (2) can be conducted to an oligomerization (not shown). The bottom of column DK1 is heated in the reboiler SV1 by means of heating steam, for example. The vapour stream BS1 is separated into the two vapour streams BS1*a* and BS1*b*. The portion BS1*b* of the vapour stream is conducted to reboiler SV2 without additional compression, where it transfers energy to the stream present therein, which is heated coming from the bottom and then returned again. BS1*a* is cooled down by means of a heat exchanger WT-1. The two streams BS1*a* and BS1*b* are run to a flash vessel, where the expansion results in a liquid phase FP1. This liquid phase is separated into the two streams FP1*a*, which is conducted to the second distillation column DK2, and FP1*b*, which is directed as reflux to the first distillation column. In distillation column 2, the streams are separated into a vapour stream BS2 which comprises at least isobutane and is withdrawn at the top of DK2, and a product stream (3) which comprises at least 1-butene is withdrawn at the bottom of DK2. Vapour stream BS2 is cooled in a heat exchanger WT-2 and run to a flash vessel, where the expansion results in a liquid phase FP2. A portion FP2*a* of phase FP2 will leave the process as isobutane stream (4), and another portion FP2*b* will be returned to the second distillation column as reflux.

Figure 2:
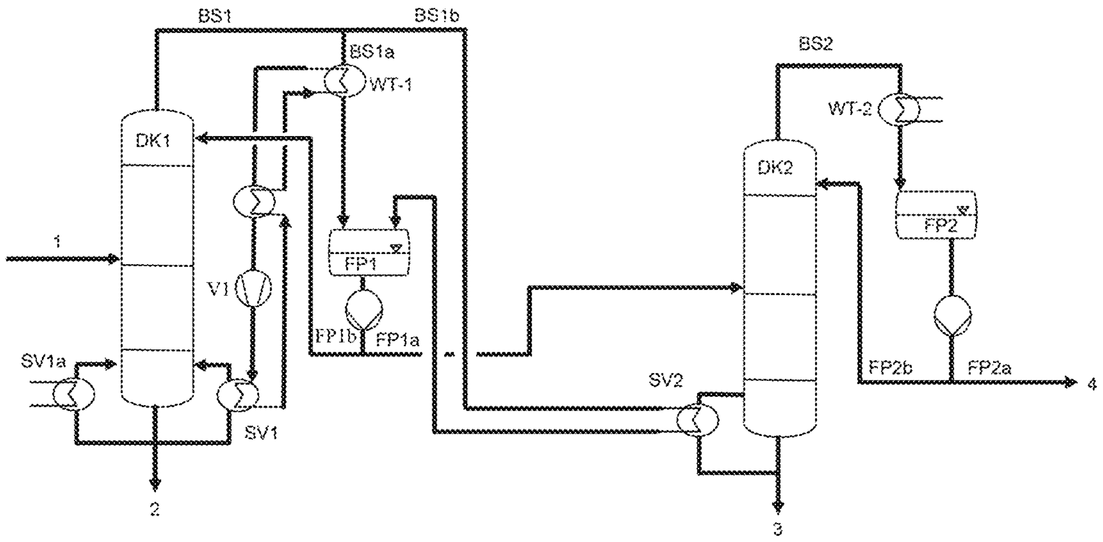
FIG. 2 shows a configuration in which, in heat exchanger WT-1, energy is transferred from stream BS1*a* to a heat transfer medium, and the heat transfer medium is compressed by a compressor V1 and then used for heating of the bottom of DK1 in reboiler SV1.

FIG. 2 shows a non-inventive embodiment which is largely identical to the embodiment represented in FIG. 1. The difference is that, in heat exchanger WT-1, energy is transferred from stream BS1*a* to a heat transfer medium, and the heat transfer medium is compressed by a compressor V1 and then used for heating of the bottom of DK1 in reboiler SV1. It is possible that an additional reboiler SV1*a* will be needed to be able to sufficiently heat the bottom of DK1.

Figure 3:
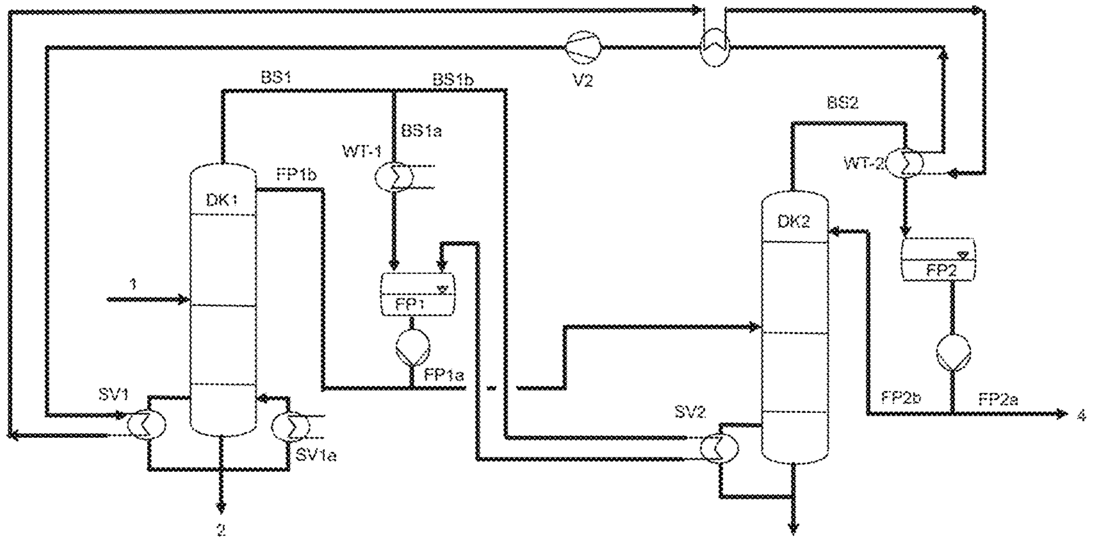
FIG. 3 shows a configuration in which, in heat exchanger WT-2, energy is transferred from stream BS2 to a heat transfer medium, and the heat transfer medium is compressed by a compressor V2 and then used for heating of the bottom of DK1 in reboiler SV1.

FIG. 3 shows a non-inventive embodiment which is largely identical to the embodiment represented in FIG. 1. The difference is that, in heat exchanger WT-2, energy is transferred from stream BS2 to a heat transfer medium, and the heat transfer medium is compressed by a compressor V2 and then used for heating of the bottom of DK1 in reboiler SV1. In the recycling operation, the recycled heat transfer medium may be used in heat exchanger WT-3 for preheating of the heat transfer medium prior to the compression. It is possible here too that an additional reboiler SV1*a* will be needed to be able to sufficiently heat the bottom of DK1.

Figure 4:
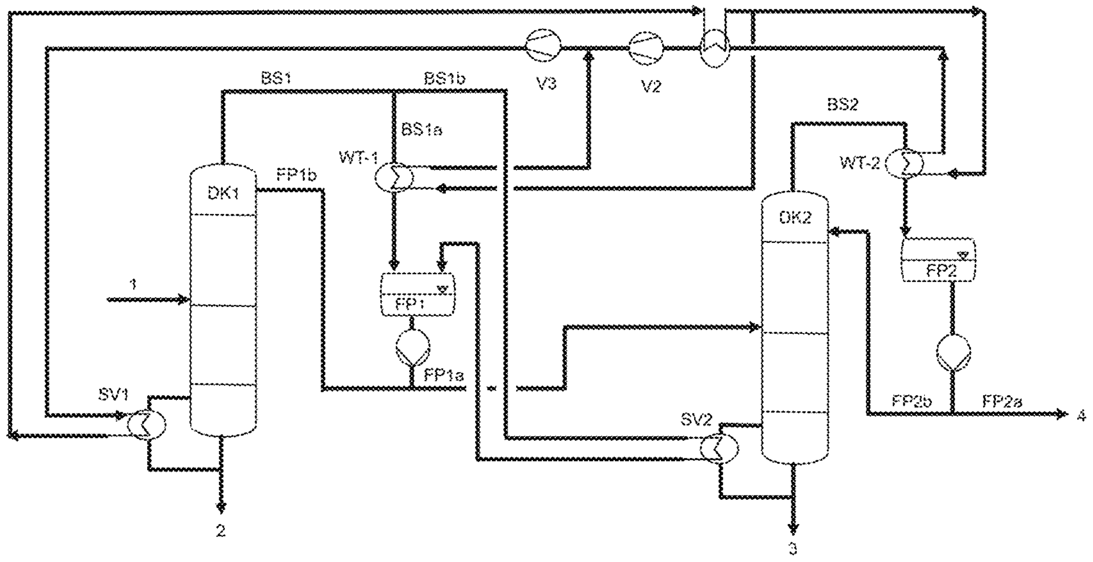
FIG. 4 shows an inventive embodiment in which the two heat pumps from FIG. 2 and FIG. 3 are combined.

FIG. 4 shows an inventive embodiment which is largely identical to the embodiments represented in FIG. 1 to FIG. 3. The difference is that the two heat pumps from FIG. 2 and FIG. 3 are combined. In heat exchanger WT-2, energy is transferred here from stream BS2 to a heat transfer medium, and the heat transfer medium is compressed in compressor V2. In heat exchanger WT-1, energy is transferred from stream BS1*a* to a heat transfer medium, and the two heat transfer media are mixed. The mixed heat transfer medium is then compressed in a compressor V3 and used for heating of the bottom of DK1 in reboiler SV1. In this embodiment, no further reboiler is required in DK1.

EXAMPLES

For all the examples that follow, a raffinate 2 stream of 55 t/h was used. The raffinate 2 stream has the following composition: 1-butene 45.1%/n-butane 22.4%/trans-2-butene 15.9%/cis-2-butene 8.9%/isobutane 7.4%/isobutene 45 ppm and water 590 ppm.

The amount of energy needed for operation of the plants detailed in the examples for separation of 1-butene from raffinate 2 was calculated by a simulation using Aspen V10. The physical data were validated by operational data and operational trials.

EXAMPLES

Example 1 (Non-Inventive)

In the embodiment according to FIG. 1, exclusively direct thermal integration between column DK1 and DK2 is implemented (as disclosed in DE 10 2005 062 700 A1). In this case, column DK1 is operated at a top pressure of 11 bar and column DK2 at a top pressure of 7 bar. It is thus possible to use a portion of vapour stream BS1 to transfer heat to DK2 via reboiler SV2. The amount of heat required for a 1-butene volume of 10.3 t/h at a purity of 99.6% 1-butene is 10.3 MW in DK2. For this purpose, a vapour stream of 125.5 t/h from DK1 is used to heat DK2. Nevertheless, it is necessary to introduce 15.9 MW in DK1 via an external heat source/medium (e.g. heating steam).

Example 2 (Non-Inventive)

The interconnection according to the invention envisages rendering the unutilized heat of condensation utilizable in DK1. Only the heat of condensation from DK1 of 4 MW is rendered utilizable here via a heat pump. Column DK1, as in Example 1, is operated at a top pressure of 11 bar abs. and a top temperature of 72 °C. Accordingly, it would be possible to utilize the heat of condensation from DK1 to evaporate methanol at 1.1 bar. The gaseous methanol is then run through a preheater in order to prevent dropletization in the downstream compressor. Methanol is brought to a pressure or temperature level such that the heat can be transferred via SV1. For this purpose, 450 kW of electrical power is required. The condensed methanol is run from SV1 through the preheating back to the condenser of DK1. The external heating output can thus be reduced from 15.9 MW to 11.45 MW. The additional external heating output is introduced via the additional evaporator SV1*a*.

Example 3 (Non-Inventive)

The interconnection according to the invention envisages rendering the unutilized heat of condensation utilizable. Only the heat of condensation from DK2 of 9.9 MW is rendered utilizable here via a heat pump. Column DK2, as in Example 1, is operated at a top pressure of 7 bar abs./top temperature of 50 °C. Methanol—as in Example 2—is unsuitable here as heat transfer medium since methanol would have to be evaporated under reduced pressure. In this example, n-pentane is used as working medium. The heat of condensation from DK2 is utilized to evaporate n-pentane at 1.4 bar abs. The gaseous n-pentane has to be subjected to superheating prior to the subsequent compression. In order to make the n-pentane utilizable for DK1, it is compressed to a pressure level of 5 bar abs. This requires an electrical power of 2000 kW. By virtue of the interconnection according to the invention, it is possible to replace 11.9 MW of external heating power with 2000 kW of electrical power. The remaining 4 MW of external heating power is introduced via the additional evaporator SV1*a*.

Example 4 (Inventive)

The interconnection according to the invention envisages rendering the unutilized heat of condensation utilizable. The heat of condensation from both columns DK1 and DK2 of 13.5 MW in total is rendered utilizable here by means of a multistage heat pump. Column DK2, as in Example 1, is operated at a top pressure of 7 bar abs./top temperature of 50 °C. The heat of condensation from DK2 is utilized to evaporate n-pentane at 1.4 bar abs. The gaseous n-pentane has to be subjected to superheating prior to the subsequent compression. The gaseous n-pentane is first compressed to a pressure level of 2.1 bar abs. with a first compressor stage. In addition, the heat of condensation from DK1 is utilized to evaporate n-pentane at 2.1 bar abs. The gaseous n-pentane stream that forms from the heat of condensation from DK1 is sucked in from a second compressor stage together with the already compressed n-pentane stream and compressed to a pressure level of 5 bar abs. A total of 3.2 MW of electrical power is required for complete electrification.

The results of Examples 1 to 4 are summarized below in Table 1.

TABLE 1

Summary of examples

| | Example 1 | Example 2 | Example 3 | Example 4 |
|---|---|---|---|---|
| External heating power [MW] | 15.9 | 11.45 | 4 | 0 |
| Electrical power for compressor [MW] | 0 | 0.55 | 2 | 3.2 |

It is found that the inventive configuration of the process for 1-butene separation has the effect that much less external heating power has to be used than in the known solution. The savings potential is thus considerable. The electrical power additionally required for operation of the compressors is much smaller and can enable C02-neutral operation when green power is used.

The invention claimed is:

1. A process for separating 1-butene from a raffinate 2 stream containing at least 1-butene, 2-butene, n-butane and isobutane in a separation unit comprising a first distillation column DK1 and a second distillation column DK2, wherein the first distillation column DK1 has at least one reboiler SV1 and a second distillation column DK2 has at least one reboiler SV2;

the at least one reboiler SV1 is fed with a stream which is withdrawn at a lower end of the first distillation column DK1 and, after passing through a respective reboiler, is guided back to the first distillation column DK1;

the at least one reboiler SV2 is fed with a stream which is withdrawn at the lower end of the second distillation column DK2 and, after passing through a respective reboiler, is guided back to the second distillation column DK2; the process comprising:

(a) directing the raffinate 2 stream to the first distillation column DK1 and separating the raffinate 2 stream in the first distillation column DK1 into at least one vapour stream BS1 which comprises at least 1-butene and isobutane and is withdrawn at a top of the first distillation column DK1, and at least one bottom stream which comprises at least 1-butene and 2-butene and is withdrawn at a bottom of the first distillation column DK1;

(b) separating the at least one vapour stream BS1 into at least two substreams comprising a substream BS1*a* and a substream BS1*b;*

(c) transferring energy from the substream BS1*a* to a liquid or gaseous heat transfer medium W, giving rise to a heat transfer medium W1;

(d) conducting a portion of the substream BS1*b* of the at least one vapour stream BS1 other than substream BS1*a* to the at least one reboiler SV2, where energy is transferred from substream BS1*b* to a stream in the at least one reboiler SV2;

(e) at least partly directing the substream BS1*a* and the substream BS1*b* to the second distillation column DK2 and separating the substream BS1*a* and the substream BS1*b* in the second distillation column DK2 into at least one vapour stream BS2 which comprises at least isobutane and is withdrawn at the top of the second distillation column DK2, and at least one product stream which comprises at least 1-butene and is withdrawn at the bottom of the second distillation column DK2;

(f) transferring energy from the at least one vapour stream BS2 to a liquid or gaseous heat transfer medium W, giving rise to a heat transfer medium W2;

(g) compressing at least a portion of the heat transfer medium W2, giving rise to a compressed heat transfer medium W2.1 at a higher pressure than heat transfer medium W2;

(h) mixing heat transfer medium W1 with heat transfer medium W2.1, giving rise to a mixed heat transfer medium W3;

(i) compressing at least a portion of the mixed heat transfer medium W3, giving rise to a compressed heat transfer medium W3.1 at a higher pressure than the mixed heat transfer medium W3;

(j) transferring energy from the compressed heat transfer medium W3.1 to a stream in the at least one reboiler SV1.

2. The process according to claim 1, further comprising: guiding the substream BS1*a* and the substream BS1*b* to a flash vessel, where they are expanded, resulting in a liquid phase FP1 of the vapour streams BS1*a* and BS1*b*.

3. The process according to claim 2, further comprising: combining the substream BS1*a* and the substream BS1*b* in the flash vessel and obtaining a common liquid phase FP1.

4. The process according to claim 3, further comprising: directing at least a portion FP1*a* of the common liquid phase FP1 to the second distillation column DK2.

5. The process according to claim 4, further comprising: returning another portion FP1*b* of the common liquid phase FP1 as reflux to the first distillation column DK1.

6. The process according to claim 1, further comprising: adjusting the temperature in the bottom of the first distillation column DK1 to a range from 40 to 110 °C.

7. The process according to claim 1, further comprising: adjusting the temperature in the bottom of the second distillation column DK2 to a range from 30 to 100 °C.

8. The process according to claim 1, wherein the first distillation column DK1 with between 150 and 300 plates.

9. The process according to claim 1, wherein distillation column DK2 with between 150 and 300 plates.

10. The process according to claim 1, further comprising: expanding the at least one vapour stream BS2 into a flash vessel, where a liquid phase FP2 is obtained.

11. The process according to claim 10, further comprising:

discharging at least a portion FP2*a* of the liquid phase FP2 from the process as product stream and returning another portion FP2*b* of the liquid phase FP2 as reflux to the second distillation column DK2.

12. The process according to claim 1, wherein the product stream contains at least 99% by weight of 1-butene.

13. The process according to claim 1, further comprising: employing only a single heat transfer medium throughout the process.

14. The process according to claim 1, further comprising: recycling the heat transfer medium W3.1 after preheating and partly directing the heat transfer medium W3.1 to c) and partly directing the heat transfer medium W3.1 to f) as heat transfer medium W.

15. The process according to claim 1, further comprising: selecting the heat transfer medium from the group consisting of water; alcohols; alcohol-water mixtures; salt-water solutions; ammonia; mineral oils; thermal oils; biological oils; and aromatic or aliphatic hydrocarbons.

* * * * *